(12) United States Patent
Yoshida et al.

(10) Patent No.: US 7,691,421 B2
(45) Date of Patent: Apr. 6, 2010

(54) FOLLICLE-STIMULATING HORMONE REDUCTION AGENT

(75) Inventors: Satoshi Yoshida, Tokyo (JP); Takahisa Ushiroyama, Takatsuki (JP)

(73) Assignee: Original Image Co., Ltd. (JP)

( * ) Notice: Subject to any disclaimer, the term of this patent is extended or adjusted under 35 U.S.C. 154(b) by 2 days.

(21) Appl. No.: 12/149,882

(22) Filed: May 9, 2008

(65) Prior Publication Data

US 2008/0254154 A1 Oct. 16, 2008

Related U.S. Application Data

(63) Continuation of application No. 10/522,658, filed as application No. PCT/JP2004/005104 on Apr. 9, 2004, now abandoned.

(30) Foreign Application Priority Data

Apr. 11, 2003 (JP) ............................... 2003-107813

(51) Int. Cl.
*A61K 36/36* (2006.01)
*A61K 36/42* (2006.01)
*A61K 36/00* (2006.01)

(52) U.S. Cl. .................. 424/738; 424/758; 424/725

(58) Field of Classification Search .................. None
See application file for complete search history.

(56) References Cited

U.S. PATENT DOCUMENTS

| | | | |
|---|---|---|---|
| 4,421,746 | A | 12/1983 | Kojima et al. |
| 4,456,597 | A | 6/1984 | Kojima et al. |
| 4,469,685 | A | 9/1984 | Kojima et al. |
| 5,753,266 | A | 5/1998 | Youssefyeh et al. |
| 5,882,672 | A | 3/1999 | Kojima et al. |
| 6,811,796 | B2 * | 11/2004 | Yoshida ............... 424/738 |
| 7,381,435 | B2 * | 6/2008 | Yoshida et al. ....... 424/739 |
| 2003/0198697 | A1 * | 10/2003 | Yoshida ............... 424/738 |
| 2008/0254154 | A1 * | 10/2008 | Yoshida et al. ....... 424/738 |

FOREIGN PATENT DOCUMENTS

| | | |
|---|---|---|
| CA | 2517136 | 9/2004 |
| EP | 0 846 466 A2 | 6/1998 |
| JP | 2813471 | 8/1998 |
| JP | 11-116498 | 4/1999 |
| JP | 2000-281584 | 10/2000 |
| JP | 2003-510344 | 3/2003 |

OTHER PUBLICATIONS

Atoyama, N. et al., "Heikeigo Futei Shusorei ni Okeru Macrophage Activating Chinese Mixed Herbs (MACH) no Men' ekikei Inshi Chosei Sayo to Rinsho Koka," Japanese Journal of Oriental Medicine, vol. 54, 2 sheets, (2003).

Atoyama, N., "Characteristics of Physical Abilities of Climacteric and Elderly Females and Their Disturbances," Nakayamashoten, Tokyo, pp. 37-76, (2001).

Atoyama, N., "Special Issue: Health Care of Middle-Aged and Elderly Females A. Climacteric Disturbance 15. The Actual State of Outpatients in Climacterium in Our Laboratory, They Gynecology, Treatment, as Outpatients in Climacterium and Postmenopause," Sanfujinkachiryo, vol. 76, pp. 206-213, (1998).

Bahmanpour, S., et al., "The effects of *Carthamus tinctorius* on sperm quality and sex hormone levels on partial sterile male rats as experimental model," 14th World Congress on In Vitro Fertilization & 3rd World Congress on In Vitro Maturation, pp. 1-2, 2007.

Dajue L., et al., "Promoting the conservation and use of underutilized and neglected crops. 7," Safflower. *Carthamus tinctorious* L., 1996, pp. 27-30.

Grant, M. H. J. et al., "Effect of Feeding High-Linoleate Safflower Seeds on Reproductive Endocrine Dynamics in Postpartum Bee Females," J. Anim. Sci. vol. 81, Suppl. 1/J. Dairy Sci., vol. 86, Suppl. 1, p. 12, 2003.

Greene, J. G., "Constructing a Standard Climacteric Scale," MATURITAS: Journal of the Climacteric & Postmenopause, vol. 29, pp. 25-31, (1998).

Igakushoin Co., Ltd., "Change of Sexual Function and Sexual Organ Form with Aging," Hyojunsanfujinkagaku: ISBN: 4260130536, pp. 23-25, (1997).

Igakushoin Co., Ltd., "Emmeniopathy B Amenorrhea," Hyojunsanfujinkagaku: ISBN: 4260130536, pp. 34-44, (1997).

Kolb, V. E., "Recent Observations on the Pathobio Chemical Mechanism Inhibiting Reproduction by Infections," Tieraerztliche Umschau, vol. 51, No. 6, pp. 371-375, (1996), Abstract.

Kondo, S., "Dentoteki Seiyaku ni yoru Hyakubyo Shuji (25) Benibana," vol. 25, No. 10, pp. 56-58, (1997).

Koyama, S., Medical Herbal Extracts of East Asia: A Materia Medica Based on the Classics: ISBN: 4-901767-04-6 C3047, Tsudo-san, Medical Yukon Co., Ltd., Kyoto, pp. 453-457, 1997.

Midori Shobo Co., Ltd., "Guideline for Treatment by Traditional Chinese Medicines, Obstetric and Gynecological Diseases, Outline of Obstetric and Gynecological Diseases," pp. 375-426, 1998.

Mizuno, M., "Psychosomatic Disorder, Climacteric Disturbance and Health Care of Middle-Aged and Elderly Women," Igakushoin Co., Ltd., Hyojunsanfujinkagaku: ISBN: 4260130536, pp. 170-175, (1997).

Naikashindangaku: ISBN: 4890132341, "Hormone Test, Nishimurashoten, Niigata," pp. 843-887, (1997).

Naitoh, Y. et al., "Clinical Effects and Hormonal Changes on the Treatment with Chinese Herb Medicine (Hachimi-Jiou-Gan) to Infertile Men," Nihon Funin Gakkai Zasshi, Vo. 35, No. 2, pp. 156-162, (1985).

(Continued)

*Primary Examiner*—Christopher R. Tate
(74) *Attorney, Agent, or Firm*—Finnegan, Henderson, Farabow, Garrett & Dunner, LLP

(57) ABSTRACT

The composition of the present invention comprising *Cucurbita moschata*, *Carthamus tinctorius*, *Plantago asiatica* and *Lonicera japonica* has a follicle-stimulating hormone reduction action. Based on this action, the composition is usable as a preventive, remedy, health food or functional food for diseases, for example, climacteric disturbance, primary hypogonadism (including ovarian hypofunction and testicular deficiency), Turner's syndrome, Klinefelter's syndrome, gonadotropin-producing tumor, testitis, and primary ovarian amenorrhea and/or hormone-producing tumor.

5 Claims, No Drawings

OTHER PUBLICATIONS

Supplemental European Search Report, mailed Nov. 8, 2007, in Application No. EP 04 726781.

Tani, T., "Efficacy and Pharmacography of Traditional Chinese Medicines, Chapter 17, Crude Drugs for Amelioration of Emmeniopathy," Nanzando co., Ltd., Tokyo, pp. 159-168, (1992).

Ushiroyama, T., et al., "A Pilot Study of a Kampo Formula, EH0202, with Intriguing Results for Menopausal Symptoms," The Journal of Alternative and Complementary Medicine, 10:2:397-399, 2004.

Ushiroyama, T., et al., "Clinical Efficacy of EH0202, a Kampo Formula, on the Health of middle-Aged Women," The American Journal of Chinese Medicine, 32:5:755-770, 2004.

Warren, P. Michelle, et al., "Use of alternative therapies in menopause," Best Practice & Research Clinical Obstetrics and Gynecology, 16:3:411-448, 2002.

Xia-Zhange, L. et al., "A 5-Day Estradiol Therapy, in Amounts Reproducing Concentrations of the Early-Mid Follicular Phase, Prevents the Activation of the Hypothalamo-Pituitary-Adrenal Axi by Interleukin-1 α in the Ovariectomized Rhesus Monkey," J. of neuroendocrinology, vol. 7, pp. 387-392, (1995).

Yanagihori, A. et al., Japanese Journal of Oriental Medicine, vol. 51, No. 6, p. 205, (2001).

Canadian Office Action (3 pages) mailed Nov. 24, 2009, in corresponding application No. 2,521,985.

* cited by examiner

FOLLICLE-STIMULATING HORMONE REDUCTION AGENT

This is a continuation of application Ser. No. 10/552,658, filed Sep. 13, 2006, now abandoned, which is the National Stage of International Application No. PCT/JP2004/005104, filed Apr. 9, 2004, which claims benefit of JP 2003-107813, filed Apr. 11, 2003, all of which are incorporated herein by reference.

TECHNICAL FIELD

The present invention relates to a follicle-stimulating hormone reduction agent characterized by comprising four kinds of crude drugs, i.e. *Cucurbita moschata*, *Carthamus tinctorius*, *Plantago asiatica* and *Lonicera japonica*.

BACKGROUND ART

Follicle-stimulating hormone (FSH) is a gonadotropic hormone (GTH) and is involved in the growth of seminiferous tubule and the promotion of semen formation in testis and, in ovary, in the growth and maturation of follicle.

The diseases associated with high amount of FSH in blood included climacteric disturbance (e.g. Hyojunsanfujinkagaku: ISBN: 4260130536, Igakushoin Co., Ltd., Change of Sexual Function and Sexual Organ Form with Aging, p. 23 to 25, 1997). Besides, there are primary hypogonadism, Turner's syndrome, Klinefelter' s syndrome, gonadotropin-producing tumor, testitis (e.g. Naikashindangaku: ISBN: 4890132341, Hormone Test, Nishimurashoten, Niigata, p. 843 to 887 1997), primary ovarian amenorrhea, hormone-producing tumor (e.g. Hyojunsanfujinkagaku: ISBN: 4260130536, Igakushoin Co., Ltd., Emmeniopathy B Amenorrhea, p. 34 to 44, 1997), etc.

Description is made on climacteric disturbance which is one of the above diseases.

Climacteric is defined in various ways but it refers to several years before and after menopause. Those diseases which appear in this period, are unbearable physically and mentally and need treatment, are called climacteric disturbance or disorder (e.g. M. Mizuno, Psychosomatic Disorder, Climacteric Disturbance and Health Care of Middle-Aged and Elderly Women, Hyojunsanfujinkagaku: ISBN: 4260130536, Igakushoin Co., Ltd., Tokyo, p. 170 to 175, 1997).

Climacteric disturbance appears in various symptoms and is largely divided into (1) dyshormonism such as metrorrhagia and atrophied vaginitis, (2) vasomotor nerve system disturbance such as burning sensation and palpitation, (3) psychomotor nerve system disturbance such as heaviness of head, headache and dizziness, (4) motor system disturbance such as stiff shoulder and lumbago, (5) digestive system disturbance such as constipation, inappetence and nausea, (6) urinary system disorder such as thamuria and sense of residual urine; (7) disorder of dermatologic system, internal medicine and urologic system such as perspiration and sense of oral dryness, (8) metabolism disturbance such as emaciation and obesity, (9) perception system such as numbness, and (10) other disturbances (e.g. Hyojunsanfujinkagaku: ISBN: 4260130536, Igakushoin Co., Ltd., Tokyo, 1997) As representative symptoms of the climacteric disturbance, there are known dizziness, indefinite complaint, headache, palpitation, etc. As psychogenic symptoms often seen in the climacteric disturbance, there can be mentioned depression, masked depression, generalized anxiety disorder, panic disorder, somatoform disorder, disorder of estrogen secretion, symptoms of the castrates, etc.

As the therapy for climacteric disturbance, various drug therapies can be mentioned.

Representative of such drug therapies are hormone replacement therapy (HRT), antianxiety drugs and anti-depressants. Meanwhile, there are times that traditional Chinese herbal medicines are used for before-menopause cases wherein menstrual cycle still remains at a certain level, or for postmenopause cases wherein HRT is contraindicated or is not desired. As main Chinese herbal medicines, there can be mentioned Toki-syakuyaku-san, Kami-syoyo-san and Keishi-bukuryo-gan (Current Diagnosis and Treatment, 12th Edition). Tsudo-san which is used only for removal of Oketsu (blood-stasis) in climacteric disturbance, contains a small amount of *Carthamus tinctorius* but the main component thereof is Japanese angelica root (e.g. T. Tani, Efficacy and Pharmacography of Traditional Chinese medicines, Chapter 17 Crude Drugs for Amelioration of Emmeniopathy, Nanzando Co., Ltd., Tokyo, p. 159 to 168, 1992; S. Koyama, Medical Herbal Extracts of East Asia: A Materia Medica Based on the Classics: ISBN: 4-901767-04-6 C3047, Tsudo-san, Medical Yukon Co., Ltd., Kyoto, p. 453 to 457). It is known that an efficacy for endocrine function is expected by use of Toki-syakuyaku-san (an agent for increasing FSH, LH and progesterone), Keishi-bukuryo-gan (an agent for increasing FSH and LH), Syakuyaku-kanzo-to (an agent for increasing progesterone and testosterone), Unkei-to (an agent for increasing LH-RH and an agent for reduction progesterone), and the like. (e.g. Guideline for Treatment by Traditional Chinese medicines, Obstetric and Gynecological Diseases, Outline of Obstetric and Gynecological Diseases, Midori Shobo Co., Ltd., Tokyo, p. 375 to 426).

Meanwhile, as to *Cucurbita moschata*, *Carthamus tinctorius*, *Plantago asiatica* and *Lonicera japonica*, respective efficacies are reported as follows. For example, it is disclosed that addition, to a feed, of at least one kind of *Cucurbita moschata*, *Plantago asiatica* and *Lonicera japonica* (particularly, a crude drug comprising these three crude drugs) can prevent, in particular, natural infection of parasites, bacteria and viruses and can achieve higher biophylaxis ability and improved meat and egg qualities. Further, it has been disclosed that a feed comprising four kinds of crude drugs, i.e. *Cucurbita moschata*, *Plantago asiatica*, *Lonicera japonica* and *Carthamus tinctorius* improves the health conditions, survival rates, quality of egg, and has anti-leucocytozoonosis effect in layers, and anti-New-Castle-disease effect and effects of the decreased numbers of enteric *Coccidium* and *Staphylococcus* in the intestine of quails (e.g. U.S. Pat. No. 5,882,672).

A method for producing an interferon inducer from the plants of the genus *Cucurbitaceae* such as pumpkin has been disclosed (e.g. U.S. Pat. No. 4,421,746). The antiviral activity and anti-tumor activity of interferon inducers extracted from the flowers of *Carthamus tinctorius* has been disclosed (e.g. U.S. Pat. No. 4,456,597). It has also been disclosed that interferon inducers may be extracted from the flowers of *Lonicera japonica*, seeds of *Plantago asiatica*, and the like, and that the extracted interferon inducers are useful for prevention and curative treatments of viral infections in humans and animals (e.g. U.S. Pat. No. 4,469,685). A macrophage activator comprising two crude drugs of *Cucurbita moschata* and *Carthamus tinctorius* has also been disclosed (e.g. Japanese Patent Laid-open No. 116498/1999). A neutrophil activator comprising four crude drugs of *Cucurbita moschata*, *Carthamus tinctorius*, *Plantago asiatica* and *Lonicera japonica* has also been disclosed (e.g. Japanese Patent Laid-open No. 281584/2000).

However, while these documents disclose the interferon inducing effects, macrophage activating effects, neutrophil activating effects, the inhibitory effects of IgE anti-body production, and the like of the crude drugs used as active components in the present invention, none of the references disclose or suggest the effect of reduction FSH level in high FSH concentration in blood.

DISCLOSURE OF THE INVENTION

The present invention aims at providing a follicle-stimulating hormone reduction agent comprising, as active components, crude drugs, in particular, *Cucurbita moschata, Carthamus tinctorius, Plantago asiatica* and*Lonicera japonica*.

As a result extensive studies on crude drugs obtained from plants, the present inventors have discovered that by administering a composition comprising *Cucurbita moschata, Carthamus tinctorius, Plantago asiatica* and *Lonicera japonica* to postmenopausal women which was high FSH concentration in blood at initiation, the amount of FSH concentration in blood suppressed significantly at 6 months after administration the composition has a surprising effect of improving subjective symptoms diagnosed by a physician as climacteric disturbance and indefinite complaint diagnosed as such by a physician. The present invention was completed based on these findings.

Hence, the present invention relates to a FSH reduction agent comprising, as active components, *Cucurbita moschata, Carthamus tinctorius, Plantago asiatica* and *Lonicera japonica*. The present invention relates particularly to the utilization of the above FSH reduction agent as a preventive or remedy for climacteric disturbance, a preventive or remedy for indefinite complaint, a preventive or remedy for ovarian hypofunction (juvenile climacteric disturbance), a preventive or remedy for testicular deficiency, and a preventive or remedy for amenorrhea; as well as to the utilization as a health food or functional food for prevention, amelioration or alleviation of climacteric disturbance, a health food or functional food for prevention, amelioration or alleviation of ovarian hypofunction (juvenile climacteric disturbance), a health food or functional food for prevention, amelioration or alleviation of testicular deficiency, and a health food or functional food for prevention, amelioration or alleviation of amenorrhea. The present invention relates further to a method of preparation of a FSH reduction agent comprising the above-mentioned active components.

Incidentally, the present invention relates to a composition which can be used together with conventional remedy for the above-mentioned diseases, etc.

BEST MODE FOR CARRYING OUT THE INVENTION

The present invention will now be described in more detail below.

In the present invention, the follicle-stimulating hormone reduction agent means a medical composition or food, particularly health food or functional food (supplement), all having effects for reduction of FSH.

Description is made on the crude drugs used in the present invention.

*Cucurbita moschata* are seeds originate from a plant belonging to the genus *Cucurbitaceae* (Japanese name: Nihon kabocha; *Cucurbita moschata* Duch). In addition, to these seeds, seeds of related plants capable of achieving the object of the present invention may be used. Although raw seeds may be used, dry seeds are preferred because of their superior storability when used as a medicine or health food. A part of seed hull may be used. *Cucurbita moschata* contain components such as cucurbitin, protein, vitamins A, $B_1$, $B_2$ and C, and further contain carotene, and the like.

*Carthamus tinctorius* is the dried tubular flower of a plant belonging, to the genus *Compositae* (known as safflower flower; *Carthamus tinctorius* L.). It contains components such as carthamin, safflor yellow, lignan and sterol.

*Plantago asiatica* belongs to the genus *Plantaginacea* (known as; Plantain; *Plantago asiatica* L.) and it's matured seeds or the entire plant may be used. It contains components such as polysaccharides, plantenolic acid, succinic acid, adenine, aucubin, plantaginin, and vitamins A and $B_1$.

*Lonicera japonica* Thunb. belongs to the genus *Gramineae* (known as honeysuckle; *Lonicera japonica* Thunb.) and its flower, bud, leaf, stem or the entire plant may be used. It contains components such as wax-like material, inositol, tannin, saponin, and lonicerin.

In the present invention, a crude powder of these crude drugs or an extract of these crude drugs obtained using water or an organic solvent may be used. Specifically, the crude drugs are used in the form of a crude powder, solvent preparation, powder preparation, compression, infusion, or the like.

The crude powder of these crude drugs can be obtained by chopping or powdering the raw plant, the material obtained by drying in the shade, or the dried material. As the organic solvent, ethanol, acetone, and the like can be used. A mixture of these organic solvents with water or a mixture of two or more organic solvents may be used. The extract can be obtained by adding the solvent in an amount of several times the crude drugs and extracting or infusing the mixture at ordinary temperature or with heating. Each of the crude drugs may be extracted separately and then mixed, or a mixture of the crude powders of several crude drugs prepared beforehand may be extracted.

The above-mentioned crude powder or extract obtained by extraction with water or an organic solvent of the crude drug may be used as it is, or prepared into various forms according to per se known methods, for use as a medical composition or food, particularly health food or functional food (supplement).

The medical composition or functional food (supplement) may be provided in the form of tablets, powder, granules, capsules, pills, or syrup for oral administration by a conventional method of preparation. During preparation, as necessary, excipients, binders, disintegrators, lubricants, buffering agents, sweeteners, stabilizers, and the like may be used. In addition, at least one inert diluent such as lactose, mannitol, glucose, hydroxypropyl cellulose, finely crystallized cellulose, starch, polyvinyl pyrrolidone, and magnesium metasilicate aluminate may be used. In addition to the inert diluents, the composition may contain additives, for example, lubricants such as magnesium stearate, starch and talc, disintegrators such as calcium cellulose glycolate, stabilizers such as lactose, and solubilizer adjuvants such as glutamic acid and aspartic acid in accordance with conventional method. Tablets or pills may be coated with a sugar or a film of a substance soluble in the stomach or intestines such as sucrose, gelatin, agar, pectin, hydroxypropyl cellulose, and hydroxypropyl methyl cellulose phthalate, as necessary.

Other additives may be added to the composition of the present invention to the extent that the effect of the crude drug active component is not adversely affected. Such additives include water-soluble vitamins such as caffeine, vitamin $B_1$, vitamin $B_2$, vitamin $B_6$, vitamin $B_{12}$, vitamin C, biotin, carnitine, panthotenic acid, nicotinic acid, and derivatives thereof, fat-soluble vitamins such as vitamin A, vitamin E, and derivatives thereof, amino acids such as taurine and arginine, oriental herbs such as perilla, licorice root, ginkgo, dandelion, chrysanthemum, ginseng, and cinnamon, western herbs such as Saw palmetto, St. John's Wort, Echinacea, aniseed, annual chamomile, rosemary, mint, Eucalyptus, lavender, rose, hibiscus, aloe, and the like.

In addition, in accordance with the method of use, other active components as oligosaccharides such as lactulose or commercial lactic acid bacteria such as bifidus may also be used.

Liquid compositions for oral administration include pharmaceutically accepted emulsifier, solvents, suspending agents, syrup, and elixirs, and contain a commonly used inert diluent such as purified water and ethanol. In addition to the inert diluent, the composition may also contain moisturizers, adjuvants such as suspending agents, sweeteners, flavorants, fragrances, and antiseptics.

In the case of a health food, the composition can be provided in the forms of a beverage or a confection such as a jelly, biscuit, cookie, or candy.

The composition of the present invention contains crude drugs of *Cucurbita moschata, Carthamus tinctorius, Plantago asiatica* and *Lonicera japonica* as active components. Preferably, the composition contains, in particular, *Cucurbita moschata* in range from 20 to 60% by weight, *Carthamus tinctorius* in range from 10 to 40% by weight, and each of the other crude drugs in range from 5 to 70% by weight.

The amount of the active components to be administered can be appropriately determined based on the age, sex, and the like of patient. Usually, in the case of an adult weighing 60 kg, the crude drugs are administered orally in a combined amount of 0.5-5 g and preferably 1-3 g on a daily basis.

EXAMPLES

The present invention will now be described in more detail below by way of Reference Examples and Examples, which should not be construed as limiting the present invention.

Reference Example 1

50 g of *Cucurbita moschata*, 3.0 g of *Carthamus tinctorius*, 1.0 g of *Plantago asiatica* and 3.0 g of *Lonicera japonica*, 67 g of lactose and 16 g of starch were mixed uniformly in a mixer. The resulting mixture was kneaded using a solution obtained by dissolving 2 g of hydroxypropyl cellulose and 5 g of capric acid triglyceride. The kneaded material was granulated using a basket type granulator (screen diameter: 1 mm); the granules were passed through a 14-mesh sieve and dried to obtain columnar granules. The granules were uniformly mixed with mannitol, hydroxypropyl cellulose, magnesium metasilicate aluminate, aspartame and a fragrance to obtain 12 chartulae of granules (Japanese Patent Laid-open No. 231584/2000).

In the following, compositions with various component ratios (% by weight) can be prepared in the same manner as that of Reference Example 1.

TABLE 1

| Formulation Example | *Cucurbita moschata* seeds | *Carthamus tinctorius* flowers | *Plantago asiatica* seeds | *Lonicera japonica* flowers |
|---|---|---|---|---|
| 1 | 60 | 20 | 10 | 10 |
| 2 | 50 | 20 | 15 | 15 |
| 3 | 50 | 10 | 25 | 15 |
| 4 | 45 | 20 | 30 | 5 |

TABLE 1-continued

| Formulation Example | *Cucurbita moschata* seeds | *Carthamus tinctorius* flowers | *Plantago asiatica* seeds | *Lonicera japonica* flowers |
|---|---|---|---|---|
| 5 | 42 | 25 | 8 | 25 |
| 6 | 40 | 30 | 20 | 10 |
| 7 | 25 | 10 | 40 | 25 |
| 8 | 25 | 15 | 38 | 22 |
| 9 | 25 | 25 | 25 | 25 |
| 10 | 25 | 25 | 5 | 45 |
| 11 | 20 | 40 | 20 | 20 |
| 12 | 20 | 10 | 60 | 10 |
| 13 | 25 | 25 | 25 | 25 |

Reference Example 2

InterPunch (registered trademark; manufactured by Sanwell Co., Ltd.) which is included the composition of the present invention.

Crude powders of crude drugs of *Cucurbita moschata, Carthamus tinctorius, Plantago asiatica*, and *Lonicera japonica* was mixed and the resulting mixture was extracted with 10 times the amount of boiling water at a temperature of 95±5° C. for 30 minutes. The extract was filtered and concentrated, followed by addition of an excipient such as reducing maltose, lactose, starch, and the like, and fragrance. The resulting material was granulated to produce fine granules.

TABLE 2

| Analysis example of nutrition per two sachets (1.5 g × 2) of InterPunch | |
|---|---|
| Calorie | 11.5 Kcal |
| Protein | 0.042 g |
| Fat | 0.003 g |
| Sugar | 2.823 g |
| Dietary fiber | 0.03 g |
| Sodium | 0.444 mg |
| Lactulose | 400 mg |
| *Cucurbita moschata* seeds | Mixed extract equivalent to 1000 mg of raw material |
| *Plantago asiatica* seeds | |
| *Carthamus tinctorius* flowers | |
| *Lonicera japonica* flowers | |
| Bifidus | 40 mg |

Example 1

Clinical Test for Patients with Indefinite Complaint of Postmenopausal Women

An investigation was made on the clinical effect and the action on immune system in cases of indefinite complaint in climacteric. The composition obtained in Reference Example 2 was administered to 32 of the patients exhibiting the indefinite complaint after menopause (with an average age of 53.0±5.1, aged from 48 to 66) for a period of six months in an amount of 6 g on a daily basis. Concentrations of LH and FSH in blood were measured and the symptoms during administration period were examined by Greene's climacteric scale and VAS (visual analog scale)

Incidentally, climacteric scales by Greene, Kupperman, et al. examine the effect on QOL of climacteric disturbance cases and the seriousness of various diseases and evaluate the seriousness. The Greene's climacteric scale was developed in order to examine the symptom of a woman in menopause and is being used clinically in order to examine the reaction directed toward the relaxation of the severity of unpleasant symptom (e.g. Green J G. Constructing a standard climacteric scale. Maturitas. 29, p. 25 to 31, 1998).

Test results:

Comparison of FSH concentrations in blood before administration and after six month administration indicates that the FSH concentration significantly reduced from 64.05±20.1 mIU/ml before administration to 52.51±18.0 mIU/ml after six month administration(P<0.05). As FSH concentration usually becomes high in climacteric, the reduction of FSH concentration is noteworthy. That is, it is known that the FSH concentration becomes physiologically high level after menopause and this change worsens the symptom of indefinite complaint; therefore, the significant reduce in FSH concentration by administration of the product of the present invention indicates contribution to amelioration of symptoms.

In the evaluation result by Greene's climacteric scale, the (total) score changed from 20.1±9.44 before administration to 12.1±8.46 after six month administration and there was a significant decrease to 60.2% (P=0.0007).

In the evaluation of subjective symptom by VAS, free evaluation of 0 to 100 (0: healthy, 100: maximum pain) was made and recorded by a patient himself or herself before administration and after six month administration, for comparison. The VAS was average 79.2±12.8 before administration and average 32.7±14.1 after six month administration and there was a significant decrease to 41.3% (P=0.001).

By administering the composition (Reference Example 2) of the present invention for a period of six months, there were significant decrease in climacteric scale and VAS to 60.2% and 41.2%, respectively, relative to the values before administration. That is, the recovering of the scales which is statistically significant decrease (0.07% and 0.01%) indicates obvious relief of patient's QOL.

Thus, it was proven that the composition (Reference Example 3) of the present invention is a FSH reduction agent and it was confirmed that the composition is effective for the treatment of climacteric disturbance or indefinite complaint.

Example 2

Safety of Health Food to Human

The formulation A of present invention composition:
Components (mixed ratio): *Cucurbita moschata* (50%) *Carthamus tinctorius* (20%), *Plantago asiatica* (15%), and *Lonicera japonica* (15%)

This formulation A of composition of the present invention was administered to seven male adults twice on a daily basis for a period of two weeks (each does comprised 1.0 g of the crude drug). Blood collection was made before administration and after one and two weeks of administration. Each blood collection was subjected to general clinical tests, i.e. hematology (number of leukocytes, number of erythrocytes, amount of hemoglobin, hematocrit value, MCV, MCH, MCHC, number of blood platelets, and leukocyte fractionation), blood biochemical tests (total protein, albumin, A/G, total bilirubin, MCV, MCH, MCHC, AST, ALT, alkali phosphatase, γ-GTP, total cholesterol, neutral fat, urea nitrogen, uric acid and creatinine), and immunobiochemical tests (nonspecific IgE, nonspecific IgG, and transferrin) as well as to medical examination by doctor's interview, auscultation and percussion by doctor, and physical tests (body temperature, pulse and blood pressure), whereby the safety of administration of the formulation A of composition of the present invention was investigated. Further, there were measured cell functions [monocyte (macrophage in the blood) phagocytic and neutrophil phagocytic activity, and NK cell activity] and cytokines (IL-2,-4,-6,-8,-10,-12, INF-β and TNF-α), whereby the effectiveness of the present health food was investigated.

The results show that during the two week period of test administration, no adverse effects in clinical test value such as harmful phenomenon considered to have been caused by ingestion of health food, regarding subjective symptoms, objective symptoms or immunobiochemical tests seemed to occur as a result of the administration of the health food of the present invention, thereby confirming the safety of the health food of the present invention. No significant change in cell function and cytokine were observed. It was judged that no measurable could be found in a healthy male at this amount and period of administration.

Example 3

Safety as Health Food

The health food was administered to a healthy male adult for a period of eight years (31 years of age at initiation). For the first two years, the subject was administered a daily average dosage equivalent to 1 g of the powder of the formulation A of composition of the present invention. Thereafter, the subject was administered a health food comprising formulation of composition of the present example at a daily average dosage equivalent to 1 g of the raw powder. The result show that no negative effects to general blood properties or health condition during the period of administration.

INDUSTRIAL APPLICABILITY

The composition of the present invention has an effect for decreasing the amount of follicle-stimulating hormone (FSH) and therefore is useful for the treatment of various diseases associated with high FSH level, such as the followings: climacteric disturbance (e.g. Hyojunsanfujinkagaku: ISBN: 4260130536, Igakushoin Co., Ltd., Change of Sexual Ability and Form of Sexual Organ with Aging, p. 23 to 25, 1997), primary hypogonadism (including ovarian hypofunction and testicular deficiency), Turner's syndrome, Klinefelter's syndrome, gonadotropin-producing tumor, testitis (e.g. Naikashindangaku: ISBN: 4890132341, Hormone Test, Nishimurashoten, Nilgata, p. 843 to 887, 1997), and primary ovarian amenorrhea and/or hormone-producing tumor (e.g. Hyojunsanfujinkagaku: ISBN: 4260130536, K.K. Igakushoin, Emmeniopathy B Amenorrhea, p. 34 to 44, 1997)

In addition, the FSH reduction agent of the present invention is useful for the treatment of, in particular, diseases of postmenopausal women said to have a high FSH level, such as climacteric disturbance or indefinite complaint.

Further, the FSH reduction agent of the present invention has improved the subjective symptoms of patients having the above-mentioned diseases and the indefinite complaint diagnosed as such by a doctor. That is, the present FSH reduction agent has improved symptoms of climacteric disturbance or indefinite complaint, i.e. fatigability, sense of fatigue, apathy, insomnia, nervousness, stiff shoulder, headache, lumbago, and/or malaise, etc.

It is reported that climacteric disturbance reduces the QOL of women significantly and has a great influence on the postmenopausal life of women (e.g. N. Atoyama, Characteristics of Physical Abilities of Climacteric and Elderly Females and Their Disturbances, Nakayamashoten, Tokyo, p. 37 to 76, 2001). It is no exaggeration to say that a key for an postmenopausal women to spend thirty years after menopause in a healthy condition lies in whether or not the women can overcome her climacteric symptom (indefinite complaint) seen in the period (e.g. N. Atoyama, Special Issue: Health Care of Middle-Aged and Elderly Females A. Climacteric Disturbance 15. The Actual State of Outpatients in Climacterium in Our Laboratory, The Gynecology, Treatment, as Outpatients in Climacterium and Postmenopause, Sanfujinkachiryo, Vol. 76, P. 206 to 213, 1998); therefore, the FSH reduction agent of the present invention can be used as an excellent preventive or remedy.

The invention claimed is:

1. A method for treating climacteric disturbance, comprising administering to a patient having climacteric disturbance a composition comprising 20% to 60% by weight *Cucurbita moschata*, 10% to 40% by weight *Carthamus tinctorius*, 5% to 70% by weight *Plantago asiatica* and 5% to 70% by weight *Lonicera japonica*.

2. A method for treating amenorrhea, comprising administering to a patient having amenorrhea a composition comprising 20% to 60% by weight *Cucurbita moschata*, 10% to 40% by weight *Carthamus tinctorius*, 5% to 70% by weight *Plantago asiatica* and 5% to 70% by weight *Lonicera japonica*.

3. A method for treating primary hypogonadism, comprising administering to a patient having primary hypogonadism a composition comprising 20% to 60% by weight *Cucurbita moschata*, 10% to 40% by weight *Carthamus tinctorius*, 5% to 70% by weight *Plantago asiatica* and 5% to 70% by weight *Lonicera japonica*.

4. The method of claim 3, wherein the primary hypogonadism is ovarian hypofunction.

5. The method of claim 3, wherein the primary hypogonadism is testicular deficiency.

* * * * *